(12) United States Patent
Shiraki et al.

(10) Patent No.: US 8,604,240 B2
(45) Date of Patent: Dec. 10, 2013

(54) METHOD FOR PRODUCING β-ALKOXYPROPIONAMIDE

(75) Inventors: Yasushi Shiraki, Ichihara (JP); Toyozo Fujioka, Ichihara (JP); Koichi Kodoi, Ichihara (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 166 days.

(21) Appl. No.: 13/133,683

(22) PCT Filed: Dec. 9, 2009

(86) PCT No.: PCT/JP2009/006708
§ 371 (c)(1),
(2), (4) Date: Jun. 9, 2011

(87) PCT Pub. No.: WO2010/067589
PCT Pub. Date: Jun. 17, 2010

(65) Prior Publication Data
US 2011/0251430 A1    Oct. 13, 2011

(30) Foreign Application Priority Data

Dec. 10, 2008 (JP) .................. 2008-314673

(51) Int. Cl.
*C07C 231/02*    (2006.01)

(52) U.S. Cl.
USPC ....................................... 564/136

(58) Field of Classification Search
USPC ....................................... 564/136
See application file for complete search history.

(56) References Cited

U.S. PATENT DOCUMENTS

| | | | | |
|---|---|---|---|---|
| 3,914,303 | A * | 10/1975 | Daniher et al. | 564/136 |
| 8,338,645 | B2 * | 12/2012 | Shiraki et al. | 564/136 |
| 2010/0076223 | A1 | 3/2010 | Shiraki et al. | |

FOREIGN PATENT DOCUMENTS

| | | |
|---|---|---|
| JP | 49-66623 | 6/1974 |
| JP | 51-125019 | 11/1976 |
| JP | 59-20258 | 2/1984 |
| JP | 2-83358 | 3/1990 |
| JP | 10-279545 | 10/1998 |
| JP | 2004-250353 | 9/2004 |
| JP | 2005-47885 | 2/2005 |
| WO | WO 2008/102615 A1 | 8/2008 |

OTHER PUBLICATIONS

English Translation of the International Preliminary Report on Patentability and Written Opinion issued Jul. 14, 2011 in Application No. PCT/JP2009/006708.
International Search Report issued Jan. 19, 2010 in Application No. PCT/JP2009/006708.

* cited by examiner

*Primary Examiner* — Shailendra Kumar
(74) *Attorney, Agent, or Firm* — Oblon, Spivak, McClelland, Maier & Neustadt, L.L.P.

(57) ABSTRACT

A method for producing a β-alkoxypropionamide including:
subjecting a β-alkoxypropionic acid ester represented by the following formula (I) and a polyol having two or more OH groups to a transesterification reaction in the presence of a basic catalyst, thereby to synthesize a transesterified polyol of a β-alkoxypropionic acid ester; and
subjecting the transesterified polyol and an amine represented by the following formula (II) to an amidation reaction, thereby to synthesize a β-alkoxypropionamide represented by the following formula (III):

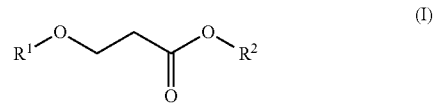

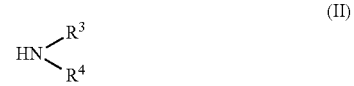

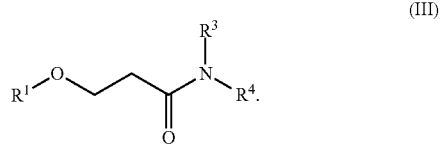

20 Claims, No Drawings

METHOD FOR PRODUCING β-ALKOXYPROPIONAMIDE

This application is a 371 of PCT/JP2009/006708, filed Dec. 9, 2009.

TECHNICAL FIELD

The invention relates to a method for producing a β-alkoxypropionamide.

BACKGROUND ART

In general, due to improved dissolving power and capability of dissolved easily in water, an amide-based organic solvent can be subjected to water rinsing, and hence has desired properties as a solvent or a detergent. It can be used as a resist peeling agent or a specific solvent for a hardly-soluble resin such as polyimide and polyamide.

Further, in recent years, since a halogen-based solvent may bring about environment pollution such as ozone layer depletion and has strong toxicity, and NMP or the like has genotoxicity, an amide-based organic solvent can be used in place of these solvents.

Conventional methods for producing this amide-based compound has problems that the production cost thereof is high due to the use of expensive materials as a starting material, the yield is low or the like, and an efficient production method has been desired.

Patent Document 1 (JP-A-S49-66623) discloses a method for the synthesis of β-alkoxy-N,N-dialkylpropionamide as an intermediate in the method for producing a N,N-dialkylpropionamide of an α,β-olefin-based unsaturated monocarboxlic acid which is used as a polymerizable monomer.

This method for the synthesis of a β-alkoxy-N,N-dialkylpropionamide is a method in which a β-alkoxypropionic acid alkyl ester and a dialkylamine are reacted to be amidated in the presence of a polyol having two adjacent hydroxyl groups.

In this method, not only a long period time (20 to 40 hours) is required for the reaction, but also the process becomes complicated due to the need of a neutralization-separation treatment during the reaction process. Accordingly, this method is difficult to be implemented on the industrial scale.

Patent Document 2 discloses a method in which a dialkylacryalamide and an aliphatic monovalent alcohol having 1 to 4 carbon atoms are reacted. According to this method, synthesis can be performed under moderate conditions. However, a dialkylacrylamide is produced through 3 to 4 steps as stated in JP-A-H10-279545. Further, since a dialkylacrylamide itself is expensive, producing a β-alkoxy-N,N-dialkylpropionamide by this method leads to an increase in cost.

Further, a method is known in which dimethylamine is reacted with an alkoxypropionyl chloride, as disclosed in Patent Document 3. For example, reacting dimethylamine with 3-ethoxy-propionylchloride in the presence of a diethyl ether solvent, 3-ethoxy-N,N-dimethylpropionamide can be synthesized.

However, due to expensive raw materials, this method cannot be said as an efficient production method, and hence, is hard to be implemented on the industrial scale.

Further, Patent Document 4 discloses a method in which a β-alkoxypropionic acid alkyl ester is once produced from an acrylic ester, and then a dialkylamine is added, whereby a β-alkoxy-N,N-dialkylpropionamide is produced. In this method, when a β-alkoxy-N,N-dialkylpropionamide is produced from a β-alkoxypropionic acid alkyl ester, a basic catalyst and a polyol are used in combination. The method disclosed in Patent Document 4 suffers a poor yield although a shorter reaction time is needed as compared with the method disclosed in Patent Document 1.

In all of these conventional methods, an amidation reaction is conducted undividedly. When a β-methoxypropionamide is synthesized from methyl β-methoxy propionate by amidation, for example, dimethylamine remains unreacted and methanol formed as a byproduct coexist. Since dimethylamine and methanol are subjected to azeotropy, it is impossible to separate them completely, resulting in an industrial disadvantage.

RELATED ART DOCUMENTS

Patent Documents

Patent Document 1: JP-A-S49-66623

Patent Document 2: JP A 2003 300329 JP Application No. 2003-300329

Patent Document 3: JP-A-S59-020258

Patent Document 4: JP A 2007 039383 JP Application No. 2007-039383

SUMMARY OF THE INVENTION

An object of the invention is to provide a method which is capable of producing a β-alkoxypropionamide efficiently.

In view of the above problems, the inventors made intensive studies on efficient production methods. As a result, the inventors have found that, by a divisional reaction in which, a β-alkoxypropionic acid ester is used as a raw material, a polyol and a basic catalyst are reacted therewith, a transesterified polyol of a β-alkoxypropionic acid ester is produced with a high selectivity, and an amine is reacted with this transesterified polyol, a β-alkoxypropionic acid ester can be amidated continuously and efficiently. The invention has been made based on this finding.

According to the invention, the following method for producing a β-alkoxypropionamide can be provided.

1. A method for producing a β-alkoxypropionamide comprising:

subjecting a β-alkoxypropionic acid ester represented by the following formula (I) and a polyol having two or more OH groups to a transesterification reaction in the presence of a basic catalyst, thereby to synthesize a transesterified polyol of a β-alkoxypropionic acid ester; and subjecting the transesterified polyol and an amine represented by the following formula (II) to an amidation reaction, thereby to synthesize a β-alkoxypropionamide represented by the following formula (III):

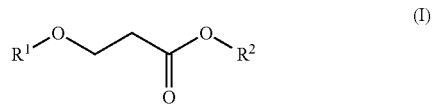

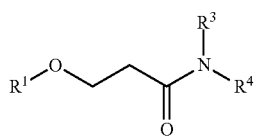 (III)

wherein R¹ and R², which may be the same or different, are an alkyl group having 1 to 8 carbon atoms, R³ and R⁴, which may be the same or different, are hydrogen, an alkyl group having 1 to 6 carbon atoms, an alkoxy group having 1 to 6 carbon atoms, an alkoxyalkyl group having 1 to 8 carbon atoms or a glycidyl group.

2. The method for producing a β-alkoxypropionamide according to 1, wherein the polyol is ethylene glycol, glycerin, diethylene glycol or propylene glycol.

3. The method for producing a β-alkoxypropionamide according to 1 or 2, wherein, in the transesterification reaction, the amount of the polyol is 0.5 to 4 moles and the amount of the basic catalyst is 0.001 to 0.1 mole, per mole of the β-alkoxypropionic acid ester.

4. The method for producing a β-alkoxypropionamide according to one of 1 to 3, wherein, in the amidation reaction, the amount of the amine represented by the formula (II) is 0.5 to 4 moles per mole of the transesterified polyol.

5. The method for producing a β-alkoxypropionamide according to one of 1 to 4, wherein the transesterification reaction is conducted at 40 to 150° C. and the amidation reaction is conducted at 30 to 120° C.

6. The method for producing a β-alkoxypropionamide according to one of 1 to 5, wherein, after the transesterification reaction, the transesterified polyol is continuously subjected to the amidation reaction without being subjected to neutralization and separation.

According to the invention, an efficient method for producing a β-alkoxypropionamide can be provided.

MODE FOR CARRYING OUT THE INVENTION

In the method of the invention, in the presence of a basic catalyst, a β-alkoxypropionic acid ester represented by the following formula (I) and a polyol having two or more OH groups are mixed to allow them to subject to a transesterification reaction, whereby a transesterified polyol of a β-alkoxypropionic acid ester is synthesized. Subsequently, an amine represented by the following formula (II) is added to this transesterified polyol to cause an amidation reaction, whereby a β-alkoxypropionamide represented by the following formula (III) is synthesized.

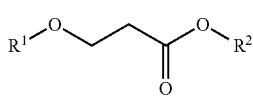 (I)

 (II)

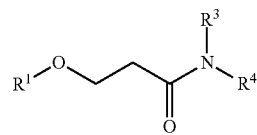 (III)

wherein R¹ and R², which may be the same or different, an alkyl group having 1 to 8 carbon atoms, R³ and R⁴, which may be the same or different, hydrogen, an alkyl group having 1 to 6 carbon atoms, an alkoxy group having 1 to 6 carbon atoms, an alkoxyalkyl group having 1 to 8 carbon atoms or a glycidyl group.

In the formula (I), R¹ and R² are independently preferably an alkyl group having 1 to 6 carbon atoms, more preferably an alkyl group having 1 to 4 carbon atoms.

In the formulas (II) and (III), R³ and R⁴ are hydrogen, an alkyl group having 1 to 6 carbon atoms, an alkoxy group having 1 to 6 carbon atoms, an alkoxyalkyl group having 1 to 8 carbon atoms or a glycidyl group.

The alkyl group having 1 to 6 carbon atoms is preferably a methyl group and an ethyl group, with a methyl group being more preferable.

The alkoxy group having 1 to 6 carbon atoms is preferably a methoxy group and an ethoxy group.

The alkoxyalkyl group having 1 to 8 carbon atoms is preferably a methoxymethyl group.

For example, a formula showing a reaction when methyl β-methoxypropionate (MPM) is used as a β-alkoxypropionic acid ester, ethylene glycol (EG) is used as a polyol, dimethylamine (DMA) is used as an amine and NaOCH₃ is used as a basic catalyst is given below.

[Transesterification Reaction]

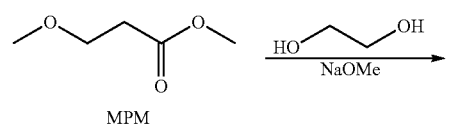

MPM

EG transesterified product of MPM

EG Transesterified Product of MPM

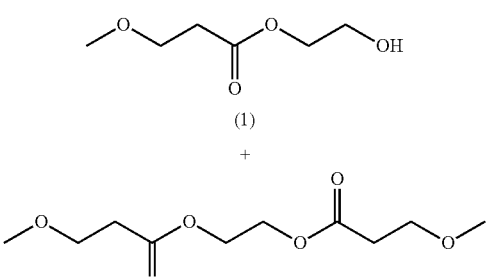

As shown by the reaction formula given above, when ethylene glycol having two OH groups and methyl β-methoxypropionate are reacted, one transesterified product of ethylene glycol as shown in formula (1) and two transesterified products of ethylene glycol as shown in formula (2) are obtained ((1):(2)=70 to 90:30 to 10).

A reaction of this transesterified product and dimethylamine is as follows:

[Amidation reaction]

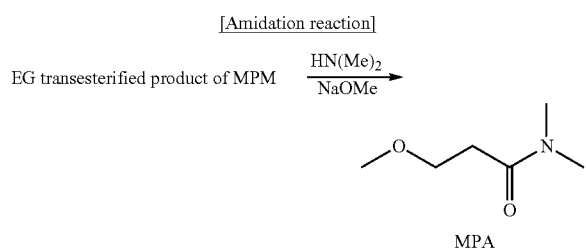

MPA

An intended β-alkoxypropioamide can be obtained from the transesterified products (1) and (2). If a transesterification reaction and an amidation reaction are conducted continuously, a catalyst used in the transesterification reaction can be used as a catalyst used in the amidation reaction.

A β-alkoxypropionic acid ester (I) can be easily obtained by a known method, for example, by a Michael addition reaction of an acrylic ester and alcohol.

As the polyol, a polyol having two or more OH groups such as glycerin, ethylene glycol, diethylene glycol and propylene glycol can be used.

There are no particular restrictions on the basic catalyst, and both an inorganic base and an organic base can be used. As the inorganic base, a hydroxide of an alkali metal such as sodium, potassium and lithium, and as the organic base, an alkoxide of the above-mentioned alkali metal, a tertiary amine, pyridine, 4-methylaminopyridine, 1,8-diazacyclo(5,4,0)undecene-7 or the like can be given. Of these, an alkoxide of an alkali metal is preferable, with potassium butoxide and sodium methoxide being particularly preferable.

In the invention, it is essential that a polyol and a basic catalyst be used in combination. A disadvantage occurs if only one of them is used. For example, if polyol alone is used, the reaction speed is lowered, resulting in the prolongation of the reaction time. If a basic catalyst alone is used, although the reaction speed is increased, the selectivity is lowered, resulting in a lowering in the yield of an intended product.

A polyol and a basic catalyst each may be used singly or in combination of two or more.

The amount of a polyol is preferably 0.5 to 4 moles, more preferably 0.8 to 2 moles, per mole of a β-alkoxypropionic acid ester. The amount of a basic catalyst is preferably 0.001 to 0.1 mole, more preferably 0.004 to 0.02 mole, per mole of a β-alkoxypropionic acid ester. If the amount of a polyol is small, selectivity is lowered, and if the amount of a polyol is too large, not only significant improvement in selectivity cannot be expected, but also a large amount of cost is incurred in separation, which is industrially unfavorable. Further, if the amount of a basic catalyst is small, the reaction speed is too low, leading to a prolonged reaction time. An excessively large amount of a basic catalyst is unfavorable since the selectivity for an intended product is lowered.

This polyol and the basic catalyst can be used in the subsequent amidation reaction as they are, whereby the subsequent amidation reaction can be conducted continuously. If a disadvantage of lowering in the reaction speed occurs in the amidation reaction, a basic catalyst can be added whenever such disadvantage occurs.

As an amine used in the amidation reaction, a dialkylamine such as dimethylamine and diethylamine can be used. They may be used as they are or may be used after diluting with an appropriate solvent.

The amount of an amine is preferably 0.5 to 4 moles, more preferably 0.8 to 2 moles, per mole of a β-alkoxypropionic acid ester. If the amount of an amine is small, an unreacted β-alkoxypropionic acid ester and a transesterified polyol remain. If the amount of an amine is too large, a large amount of cost is incurred for the recovery of an amine.

The reaction temperature of the polyol transesterification reaction is preferably 40 to 150° C., more preferably 60 to 120° C., and further preferably 80 to 110° C. If the temperature is too low, the reaction speed is lowered, and as a result, a long period of time is required to obtain a high conversion ratio. On the other hand, if the temperature is too high, the amount of a byproduct such as a heavy material is increased, resulting in a poor yield.

The reaction temperature of the amidation reaction is preferably 30 to 120° C., more preferably 40 to 100° C., and further preferably 40 to 80° C. If the temperature is too low, not only the reaction speed is lowered, but also unreacted transesterified polyol remains, the separation of which requires a great amount of labor. If the temperature is too high, the amount of a decomposed product is disadvantageously increased.

For example, when β-methoxy-N,N-dimethylpropionamide is formed, dimethylacrylamide (DMAA) or the like is formed as a byproduct by decomposition, not only the yield is lowered, but also disadvantages such as blockage of a pipe or the like occur due to high polymerization capability of DMAA.

As in the case of the invention, when a β-alkoxypropionamide is produced from a β-alkoxypropionic acid ester, by conducting the so-called divisional reaction in which a polyol transesterification reaction is conducted in the co-presence of a polyol and a basic catalyst, and subsequently, an amidation reaction is conducted with an amine, not only the yield is increased, but also the amount of an unreacted product (raw materials, transesterified polyol) is decreased, whereby a high selectivity is attained with a smaller amount of a byproduct.

In addition, there are advantages that, for example, when methyl β-methoxypropionate and dimethylamine are used, if methanol, which is formed as a byproduct in a transesterification reaction, is recovered as it is after the transesterification reaction by the divisional reaction, unreacted dimethylamine in a subsequent amidation reaction can be easily recovered since no methanol coexists.

In addition, a reaction can be conducted under mild conditions, operation can be conducted continuously without neutralization and separation of formed products, which poses significant industrial advantage.

EXAMPLES

Example 1

A polyol transesterification reaction and an amidation reaction were divisionally conducted as follows (divisional reaction).

To a 100 ml-SUS autoclave provided with a pressure gauge and a stirrer, 23.63 g (0.2 mole) of methyl β-methoxypropionate (MPM), 18.62 g (0.3 mole) of ethylene glycol and 0.065 g (0.0012 mole) of sodium methoxide (NaOMe) as a basic catalyst were added. The autoclave was immersed in an oil bath under heating at 80° C., and stirring was started. After conducting stirring for 4 hours, the autoclave was taken out from the oil bath, and quenched to around room temperature in an ice water bath. Part of the thus generated liquid was taken out, and subjected to a gas chromatographic (GC) analysis.

Thereafter, 10.82 g (0.24 mole) of liquefied dimethylamine (DMA) was put in a cooled autoclave. The autoclave was immersed again in an oil bath under heating at 60° C., and stirring was started. The stirring was conducted for 6 hours. Thereafter, the autoclave was taken out from the oil bath, and quenched to room temperature in an ice water bath. The reaction liquid was taken out, and subjected to a GC analysis.

In the reaction liquid, in addition to intended β-methoxy-N,N-dimethylpropionamide (MPA), unreacted methyl β-methoxypropionate, an unreacted transesterified product, APA, DMAA, MPAc with the following structures, and others (light or heavy material) were formed as byproducts.

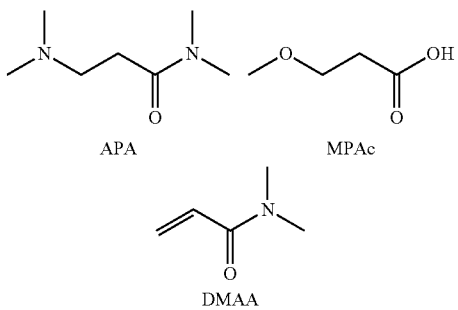

APA      MPAc

DMAA

The reaction results are given below. The results of the amidation reaction are the reaction performance after the transesterification reaction-amidation reaction.

Polyol Transesterification Reaction
    MPM conversion ratio: 69.3%
    Selectivity for transesterified polyol: 93.8%
    Selectivity for others: 6.2%
Amidation Reaction
    MPM conversion ratio: 97.1%
    Selectivity: MPA (97.1%), Transesterified polyol (0.0%), APA (0.8%), DMAA+MPAc (0.8%), Others (1.3%)

Example 2

A reaction was conducted in the same manner as in Example 1, except that glycerin was used as the polyol instead of ethylene glycol, the amount of glycerin was changed to 22.1 g (0.24 mole) and the transesterification reaction was conducted at 60° C. for 4 hours. The reaction results are shown below.

Polyol Transesterification Reaction
    MPM conversion ratio: 56.8%
    Selectivity for transesterified polyol: 71.5%
    Selectivity for others: 28.5%
Amidation Reaction
    MPM conversion ratio: 93.7%
    Selectivity: MPA (95.2%), Transesterified polyol (0.0%), APA (1.3%), DMAA+MPAc (1.8%), Others (1.7%)

Example 3

A reaction was conducted in the same manner as in Example 1, except that diethylene glycol was used as the polyol instead of ethylene glycol, the amount of diethylene glycol was changed to 25.47 g (0.24 mole) and the amount of dimethylamine used for the amidation reaction was changed to 16.23 g (0.36 mole). The reaction results are shown below.

Polyol Transesterification Reaction
    MPM conversion ratio: 52.4%
    Selectivity for transesterified polyol: 94.2%
    Selectivity for others: 5.8%
Amidation Reaction
    MPM conversion ratio: 96.3%
    Selectivity: MPA (97.3%), Transesterified polyol (0.0%), APA (0.6%), DMAA+MPAc (1.1%), Others (1.0%)

Example 4

A reaction was conducted in the same manner as in Example 1, except that 1,2-propanediol was used as the polyol instead of ethylene glycol, the amount of 1,2-propanediol was changed to 18.26 g (0.24 mole) and the amount of dimethylamine used for the amidation reaction was changed to 12.62 g (0.28 mole). The reaction results are shown below.

Polyol Transesterification Reaction
    MPM conversion ratio: 58.6%
    Selectivity for transesterified polyol: 78.9%
    Selectivity for others: 21.1%
Amidation Reaction
    MPM conversion ratio: 95.2%
    Selectivity: MPA (97.2%), Transesterified polyol (0.0%), APA (0.6%), DMAA+MPAc (1.1%), Others (1.1%)

Example 5

A reaction was conducted in the same manner as in Example 1, except that 1,3-propanediol was used as the polyol instead of ethylene glycol, the amount of 1,3-propanediol was changed to 18.26 g (0.24 mole) and the amount of dimethylamine used for the amidation reaction was changed to 12.62 g (0.28 mole). The reaction results are shown below.

Polyol Transesterification Reaction
    MPM conversion ratio: 71.7%
    Selectivity for transesterified polyol: 80.7%
    Selectivity for others: 19.3%
Amidation Reaction
    MPM conversion ratio: 97.2%
    Selectivity: MPA (96.9%), Transesterified polyol (0.0%), APA (0.7%), DMAA+MPAc (1.2%), Others (1.2%)

Comparative Example 1

In Examples 1 to 5, the polyol addition reaction and the amidation reaction were conducted separately (divisional reaction). In this comparative example, methyl β-methoxypropionate, ethylene glycol and dimethylamine were simultaneously placed in an autoclave to allow the polyol addition reaction and the amidation reaction to be conducted simultaneously (batch reaction). Specifically, the reaction was conducted as follows.

To a 100 ml-SUS autoclave provided with a pressure gauge and a stirrer, 23.63 g (0.2 mole) of methyl β-methoxypropionate, 24.83 g (0.4 mole) of ethylene glycol and 0.065 g (0.0012 mole) of sodium methoxide (NaOMe) as a basic catalyst were added. To this autoclave, 10.82 g (0.24 mole) of liquefied dimethylamine was added, and the autoclave was then immersed in an oil bath under heating at 60° C., and stirring was started. After conducting stirring for 8 hours, the autoclave was taken out from the oil bath, and quenched to room temperature in an ice water bath. The generated liquid was taken out, and subjected to a GC analysis. The reaction results are shown below.

Amidation Reaction
  MPM conversion ratio: 96.1%
  Selectivity: MPA (95.1%), Transesterified polyol (0.8%), APA (0.4%), DMAA+MPAc (2.7%), Others (1.0%)

Comparative Example 2

A reaction was conducted in the same manner as in Comparative Example 1, except that 36.84 g (0.4 mole) of glycerin was added as the polyol instead of ethylene glycol. The reaction results are shown below.
Amidation Reaction
  MPM conversion ratio: 91.1%
  Selectivity: MPA (89.8%), Transesterified polyol (6.2%), APA (0.9%), DMAA+MPAc (2.1%), Others (1.0%)

Comparative Example 3

A reaction was conducted in the same manner as in Comparative Example 1, except that 25.47 g (0.24 mole) of diethylene glycol was added as the polyol instead of ethylene glycol and the amount of dimethylamine was changed to 16.23 g (0.36 mole). The reaction results are shown below.
Amidation Reaction
  MPM conversion ratio: 95.8%
  Selectivity: MPA (92.8%), Transesterified polyol (1.2%), APA (1.9%), DMAA+MPAc (2.6%), Others (1.5%)

Comparative Example 4

A reaction was conducted in the same manner as in Comparative Example 1, except that NaOMe as the basic catalyst was not added, the reaction was conducted at 80° C. for 20 hours and the amount of dimethylamine was changed to 16.23 g (0.36 mole). The reaction results are shown below.
Amidation Reaction
  MPM conversion ratio: 83.4%
  Selectivity: MPA (95.4%), Transesterified polyol (0.9%), APA (0.7%), DMAA+MPAc (2.0%), Others (1.0%)

Comparative Example 5

A reaction was conducted in the same manner as in the transesterification reaction in Example 2, except that 0.20 g (0.002 mole) of sulfuric acid ($H_2SO_4$) was used as the catalyst instead of the basic catalyst NaOMe and the transesterification reaction was conducted at 110° C. for 4 hours. The reaction results are shown below.

Polyol Transesterification Reaction
  MPM conversion ratio: 69.6%
  Selectivity for transesterified polyol (58.9%)
  Selectivity for others: 41.1%
(Effects of Divisional Reaction)

The divisional reaction (the polyol transesterification reaction and the amidation reaction were conducted separately) and the batch reaction (the polyol transesterification reaction and the amidation reaction were conducted simultaneously) are compared.

Since the reaction performance varies depending on the kind of polyol, the reaction performance of the amidation reaction is compared between Example 1 and Comparative Example 1, between Example 2 and Comparative Example 2 and between Example 3 and Comparative Example 3.

As is apparent from Tables 1 and 2, in the divisional reaction, the MPM conversion ratio and the MPA selectivity were higher, and as a result, the yield was high, as compared with the batch reaction. In particular, in the divisional reaction, there was almost no remaining transesterified polyol.
(Effects of Type of Polyol)

Five kinds of polyol were used in Examples. In each Example, a high yield was obtained, and there was almost no remaining transesterified polyol.
(Effects of Addition of Catalyst)

NaOMe was used as the basic catalyst in Examples. No catalyst was used in Comparative Example 4.

Ethylene glycol was used as the polyol in Comparative Example 4. Comparison was made between Comparative Example 4 and Comparative Example 1 in which ethylene glycol was used similarly and the catalyst was added. It was revealed that, if no catalyst was added, a prolonged period of time was required to obtain an almost equivalent selectivity, and even after the lapse of 20 hours, the conversion ratio was low.
(Influence of Type of Catalyst)

In Patent Document 1 (JP-A-S49-66623), an acid catalyst ($H_2SO_4$) was used for the production of a polyol ester intermediate. In Comparative Example 5, $H_2SO_4$ was used as the acid catalyst. In Example 2, a reaction was conducted under the same conditions except that the catalyst was changed to a basic catalyst.

As a result of comparison between Example 2 and Comparative Example 5, it is revealed that, if a basic catalyst is used, as compared with the case where an acid catalyst is used, although the conversion ratio is slightly low, the selectivity for a transesterified product is high, the amount of a byproduct such as a heavy material is small, whereby a high reaction efficiency can be attained.

TABLE 1

| | | Example 1 | | Example 2 | | Example 3 | | Example 4 | | Example 5 | |
|---|---|---|---|---|---|---|---|---|---|---|---|
| | | Reaction | | | | | | | | | |
| | | Trans-esterification | Amidation | Trans-esterification | Amidation | Trans-esterification | Amidation | Trans-esterification | Amidation | Trans-esterification | Amidation |
| Reaction mode | Divisional/Batch | Divisional | | Divisional | | Divisional | | Divisional | | Divisional | |
| Temperature | (° C.) | 80 | 60 | 60 | 60 | 80 | 60 | 80 | 60 | 80 | 60 |
| Time | (h) | 4 | 6 | 4 | 6 | 4 | 6 | 4 | 6 | 4 | 6 |
| | | Amount of materials | | | | | | | | | |
| MPM | (g) | 23.63 | — | 23.63 | — | 23.63 | — | 23.63 | — | 23.63 | — |
| | (M) | 0.2 | — | 0.2 | — | 0.2 | — | 0.2 | — | 0.2 | — |
| Glycerine | (g) | — | — | 22.1 | — | — | — | — | — | — | — |
| | (M) | — | — | 0.24 | — | — | — | — | — | — | — |
| Ethylene glycol | (g) | 18.62 | — | — | — | — | — | — | — | — | — |
| | (M) | 0.3 | — | — | — | — | — | — | — | — | — |

TABLE 1-continued

|  |  | Example 1 | | Example 2 | | Example 3 | | Example 4 | | Example 5 | |
|---|---|---|---|---|---|---|---|---|---|---|---|
|  |  | \multicolumn{10}{c}{Reaction} |
|  |  | Trans-esteri-fication | Amida-tion | Trans-esteri-fication | Amida-tion | Trans-esteri-fication | Amida-tion | Trans-esteri-fication | Amida-tion | Trans-esteri-fication | Amida-tion |
| Diethylene glycol | (g) | — | — | — | — | 25.47 | — | — | — | — | — |
|  | (M) | — | — | — | — | 0.24 | — | — | — | — | — |
| 1,2-Propanediol | (g) | — | — | — | — | — | — | 18.26 | — | — | — |
|  | (M) | — | — | — | — | — | — | 0.24 | — | — | — |
| 1,3-Propanediol | (g) | — | — | — | — | — | — | — | — | 18.26 | — |
|  | (M) | — | — | — | — | — | — | — | — | 0.24 | — |
| NaOMe | (g) | 0.065 | — | 0.065 | — | 0.065 | — | 0.065 | — | 0.065 | — |
|  | (M) | 0.0012 | — | 0.0012 | — | 0.0012 | — | 0.0012 | — | 0.0012 | — |
| $H_2SO_4$ | (g) | — | — | — | — | — | — | — | — | — | — |
|  | (M) | — | — | — | — | — | — | — | — | — | — |
| DMA | (g) | — | 10.82 | — | 10.82 | — | 16.23 | — | 12.62 | — | 12.62 |
|  | (M) | — | 0.24 | — | 0.24 | — | 0.36 | — | 0.28 | — | 0.28 |
|  |  | \multicolumn{10}{c}{Molar ratio of materials} |
| Polyol/MPM | (—) | 1.5 | — | 1.2 | — | 1.2 | — | 1.2 | — | 1.2 | — |
| Catalyst/MPM | (—) | 0.006 | — | 0.006 | — | 0.006 | — | 0.006 | — | 0.006 | — |
| DMA/MPM | (—) | — | 1.2 | — | 1.2 | — | 1.8 | — | 1.4 | — | 1.4 |
|  |  | \multicolumn{10}{c}{Results} |
| Conversion ratio (%) | MPM | 69.3 | 97.1 | 56.8 | 93.7 | 52.4 | 96.3 | 58.6 | 95.2 | 71.7 | 97.2 |
| Selectivity (%) | MPA | — | 97.1 | — | 95.2 | — | 97.3 | — | 97.2 | — | 96.9 |
|  | Transesterified product | 93.8 | 0.0 | 71.5 | 0.0 | 94.2 | 0.0 | 78.9 | 0.0 | 80.7 | 0.0 |
|  | APA | — | 0.8 | — | 1.3 | — | 0.6 | — | 0.6 | — | 0.7 |
|  | DMAA + MPAc | — | 0.8 | — | 1.8 | — | 1.1 | — | 1.1 | — | 1.2 |
|  | Others | 6.2 | 1.3 | 28.5 | 1.7 | 5.8 | 1.0 | 21.1 | 1.1 | 19.3 | 1.2 |

TABLE 2

|  |  | Comparative Example 1 | Comparative Example 2 | Comparative Example 3 | Comparative Example 4 | Comparative Example 5 |
|---|---|---|---|---|---|---|
|  |  | \multicolumn{5}{c}{Reaction} |
|  |  | Transesteri-fication Amidation | Transesteri-fication Amidation | Transesteri-fication Amidation | Transesteri-fication Amidation | Transesteri-fication |
| Reaction mode | Divisional/Batch | Batch | Batch | Batch | Batch | Divisional |
| Temperature | (° C.) | 60 | 60 | 60 | 80 | 110 |
| Time | (h) | 8 | 8 | 8 | 20 | 4 |
|  |  | \multicolumn{5}{c}{Amount of materials} |
| MPM | (g) | 23.63 | 23.63 | 23.63 | 23.63 | 23.63 |
|  | (M) | 0.2 | 0.2 | 0.2 | 0.2 | 0.2 |
| Glycerine | (g) | — | 36.84 | — | — | 22.1 |
|  | (M) | — | 0.4 | — | — | 0.24 |
| Ethylene glycol | (g) | 24.83 | — | — | 24.83 | — |
|  | (M) | 0.4 | — | — | 0.4 | — |
| Diethylene glycol | (g) | — | — | 25.47 | — | — |
|  | (M) | — | — | 0.24 | — | — |
| 1,2-Propanediol | (g) | — | — | — | — | — |
|  | (M) | — | — | — | — | — |
| 1,3-Propanediol | (g) | — | — | — | — | — |
|  | (M) | — | — | — | — | — |
| NaOMe | (g) | 0.065 | 0.065 | 0.065 | — | — |
|  | (M) | 0.0012 | 0.0012 | 0.0012 | — | — |
| $H_2SO_4$ | (g) | — | — | — | — | 0.20 |
|  | (M) | — | — | — | — | 0.002 |
| DMA | (g) | 10.82 | 10.82 | 16.23 | 16.23 | — |
|  | (M) | 0.24 | 0.24 | 0.36 | 0.36 | — |
|  |  | \multicolumn{5}{c}{Molar ratio of materials} |
| Polyol/MPM | (—) | 2 | 2 | 1.2 | 2 | 1.2 |
| Catalyst/MPM | (—) | 0.006 | 0.006 | 0.006 | — | 0.01 |
| DMA/MPM | (—) | 1.2 | 1.2 | 1.8 | 1.8 | — |

TABLE 2-continued

|  |  | Comparative Example 1 | Comparative Example 2 | Comparative Example 3 | Comparative Example 4 | Comparative Example 5 |
|---|---|---|---|---|---|---|
|  |  |  |  | Reaction |  |  |
|  |  | Transesterification Amidation | Transesterification Amidation | Transesterification Amidation | Transesterification Amidation | Transesterification |
|  |  |  | Results |  |  |  |
| Conversion ratio (%) | MPM | 96.1 | 91.1 | 95.8 | 83.4 | 69.6 |
| Selectivity (%) | MPA | 95.1 | 89.8 | 92.8 | 95.4 | — |
|  | Transesterified product | 0.8 | 6.2 | 1.2 | 0.9 | 58.9 |
|  | APA | 0.4 | 0.9 | 1.9 | 0.7 | — |
|  | DMAA + MPAc | 2.7 | 2.1 | 2.6 | 2.0 | — |
|  | Others | 1.0 | 1.0 | 1.5 | 1.0 | 41.1 |

INDUSTRIAL APPLICABILITY

According to the production method of the invention, a β-alkoxypropionamide can be produced efficiently. A β-alkoxypropionamide is effective as a solvent.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in its entirety.

The invention claimed is:

1. A method for producing a β-alkoxypropionamide, the method comprising:

subjecting a β-alkoxypropionic acid ester of formula (I)

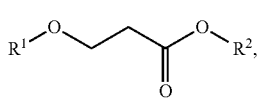 (I)

and a polyol having two or more OH groups to a transesterification reaction in the presence of a basic catalyst, thereby synthesizing a transesterified polyol of a β-alkoxypropionic acid ester; and subjecting the transesterified polyol and an amine of formula (II)

 (II)

to an amidation reaction, thereby synthesizing a β-alkoxypropionamide of formula (III):

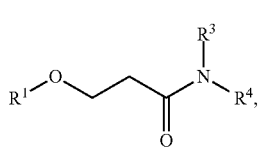 (III)

wherein $R^1$ and $R^2$, which are the same or different, are an alkyl group having 1 to 8 carbon atoms, $R^3$ and $R^4$, which are the same or different, are hydrogen, an alkyl group having 1 to 6 carbon atoms, an alkoxy group having 1 to 6 carbon atoms, an alkoxyalkyl group having 1 to 8 carbon atoms, or a glycidyl group.

2. The method of claim 1, wherein the polyol is ethylene glycol, glycerin, diethylene glycol, or propylene glycol.

3. The method of claim 1, wherein, in the transesterification reaction, an amount of the polyol is 0.5 to 4 moles and an amount of the basic catalyst is 0.001 to 0.1 mole, per mole of the β-alkoxypropionic acid ester.

4. The method of claim 1, wherein, in the amidation reaction, an amount of the amine of formula (II) is 0.5 to 4 moles per mole of the transesterified polyol.

5. The method of claim 1, wherein the transesterification reaction is conducted at 40 to 150° C. and the amidation reaction is conducted at 30 to 120° C.

6. The method of claim 1, wherein, after the transesterification reaction, the transesterified polyol is continuously subjected to the amidation reaction without being subjected to neutralization and separation.

7. The method of claim 2, wherein, in the transesterification reaction, an amount of the polyol is 0.5 to 4 moles and an amount of the basic catalyst is 0.001 to 0.1 mole, per mole of the β-alkoxypropionic acid ester.

8. The method of claim 2, wherein, in the amidation reaction, an amount of the amine of formula (II) is 0.5 to 4 moles per mole of the transesterified polyol.

9. The method of claim 3, wherein, in the amidation reaction, an amount of the amine of formula (II) is 0.5 to 4 moles per mole of the transesterified polyol.

10. The method of claim 2, wherein the transesterification reaction is conducted at 40 to 150° C. and the amidation reaction is conducted at 30 to 120° C.

11. The method of claim 3, wherein the transesterification reaction is conducted at 40 to 150° C. and the amidation reaction is conducted at 30 to 120° C.

12. The method of claim 4, wherein the transesterification reaction is conducted at 40 to 150° C. and the amidation reaction is conducted at 30 to 120° C.

13. The method of claim 2, wherein, after the transesterification reaction, the transesterified polyol is continuously subjected to the amidation reaction without being subjected to neutralization and separation.

14. The method of claim 3, wherein, after the transesterification reaction, the transesterified polyol is continuously subjected to the amidation reaction without being subjected to neutralization and separation.

15. The method of claim 4, wherein, after the transesterification reaction, the transesterified polyol is continuously subjected to the amidation reaction without being subjected to neutralization and separation.

16. The method of claim 5, wherein, after the transesterification reaction, the transesterified polyol is continuously subjected to the amidation reaction without being subjected to neutralization and separation.

17. The method of claim 1, wherein the polyol is ethylene glycol.

18. The method of claim 1, wherein the polyol is glycerin.

19. The method of claim 1, wherein the polyol is diethylene glycol.

20. The method of claim 1, wherein the polyol is propylene glycol.

* * * * *